(12) United States Patent
Mesa et al.

(10) Patent No.: US 7,329,240 B2
(45) Date of Patent: Feb. 12, 2008

(54) PROTECTIVE PACKAGING FOR MEDICAMENT DISPENSER

(75) Inventors: C Michael Mesa, Boyds, MD (US);
Daniel Jendrycki, Wildwood, MI (US);
Cynthia J. Good, Lake Sherwood, MI (US)

(73) Assignee: Meridian Medical Technologies, Inc., Columbia, MD (US)

( * ) Notice: Subject to any disclaimer, the term of this patent is extended or adjusted under 35 U.S.C. 154(b) by 248 days.

(21) Appl. No.: 10/738,985

(22) Filed: Dec. 19, 2003

(65) Prior Publication Data

US 2004/0182736 A1  Sep. 23, 2004

Related U.S. Application Data

(60) Provisional application No. 60/437,354, filed on Jan. 2, 2003.

(51) Int. Cl.
*A61M 5/20* (2006.01)

(52) U.S. Cl. ............... 604/138; 604/403; 604/408; 604/410

(58) Field of Classification Search ............ 604/138, 604/408, 403, 410; 206/438, 205; 383/106
See application file for complete search history.

(56) References Cited

U.S. PATENT DOCUMENTS

| | | | | |
|---|---|---|---|---|
| 4,150,744 A | * | 4/1979 | Fennimore | 206/205 |
| 4,509,197 A | * | 4/1985 | Long | 383/106 |
| 5,092,843 A | | 3/1992 | Monroe et al. | |
| 5,352,466 A | * | 10/1994 | Delonis | 426/123 |
| 5,896,989 A | * | 4/1999 | Ropiak et al. | 206/438 |

FOREIGN PATENT DOCUMENTS

EP  0628407 A  12/1994

* cited by examiner

*Primary Examiner*—Kevin C. Sirmons
*Assistant Examiner*—Phillip Gray
(74) *Attorney, Agent, or Firm*—Jones Day (57) ABSTRACT

A protective package for a medicament dispenser has an inner protective layer and an outer chemical barrier layer. The protective package also includes at least one reinforcing layer secured to the outer chemical barrier layer. At least one light inhibiting layer is further provided to limit the transmission of light through the package.

65 Claims, 6 Drawing Sheets

PROTECTIVE PACKAGING FOR MEDICAMENT DISPENSER

CROSS REFERENCE TO RELATED APPLICATION

This application relates to and claims priority to U.S. Provisional Patent Application No. 60/437,354 filed on Jan. 2, 2003.

FIELD OF THE INVENTION

The present invention relates to a protective packaging for an article. In particular, the present invention relates to protective packaging for a medicament dispenser to protect the medicament dispenser from exposure to chemical agents (i.e., chemical warfare agents) and other potential contaminants. The present invention further relates to a protective packaging for a light sensitive medicament wherein the protective packaging prevents the transmission of light through the package to the medicament dispenser housed therein.

OBJECTS OF THE INVENTION

It is an object of the present invention to provide a protective package for a medicament dispenser.

It is another object of the present invention to provide a protective package for a self-administering medicament dispenser that permits easy opening by the user.

It is another object of the present invention to provide a package for a medicament dispenser that protects the dispenser from exposure to chemical agents when the package is exposed to the same.

It is another object of the present invention to provide a package for a medicament dispenser that protects the dispenser from exposure to a caustic agent when the package is undergoing a decontamination procedure.

It is an object of the present invention to a provide a package that protects a medicament dispenser containing a light sensitive medicament from exposure to light.

It is another object of the present invention to provide a package that prevents exposing a medicament dispenser containing a light sensitive medicament to light while permitting the viewing of a label on the medicament dispenser.

It is another object of the present invention to provide a multilayer package to provide protection for a medicament dispenser from exposure to chemical contaminants.

It is yet another object of the present invention to provide a protective package containing at least one reinforcing layer.

It is still another object of the present invention to provide a protective package for a medicament dispenser that can be easily carried by a soldier in the field.

It is another object of the present invention to provide a protective package for a medicament dispenser that can be easily opened such that a soldier may readily access the medicament dispenser when exposed to chemical or biological agents.

It is another object of the present invention to provide a package that permits the viewing of specific information on a label relating to a medicament while limiting the exposure of the medicament to light.

It is another object of the present invention to provide a protective package that is capable of withstanding a decontamination procedure including exposure to caustic chemical agents without breaking down.

Additional objects and advantages of the invention are set forth, in part, in the description which follows, and, in part, will be apparent to one of ordinary skill in the art from the description and/or practice of the invention.

SUMMARY OF THE INVENTION

In response to the foregoing challenges, applicants have developed an innovative protective package that minimizes exposure of the medication to light while providing adequate protection when exposed to chemical contaminants, chemical warfare agents or other potential harmful contaminants.

The present invention is directed to a protective package for a medicament dispenser. It is contemplated that the protective package in accordance with the present invention may be used in connection with a medicament dispenser, which includes, but is no limited to auto-injectors, syringes and other means for administering medicaments. The medicament dispenser is capable of storing at least one medicament. It is preferable that the medicament dispenser stores two medicaments. The medicaments may include a pair of liquid medicaments or a dry medicament mixed with a liquid medicament during the administering operation. The medicament dispenser may also be a self administering medicament dispenser. Although the protective package is disclosed in connection with a medicament dispenser, the present invention is not intended to be so limited; rather, it is contemplated that the protective package disclosed herein may be used with any type of article that may be used in the field and requires protection from exposure to light and/or hazardous chemical agents.

In accordance with one embodiment of the present invention, the protective package includes an inner protective layer surrounding the medicament dispenser. The inner protective layer is preferably formed from a polyethylene material. The protective package further includes an outer chemical barrier layer secured to the inner protective layer. The outer chemical barrier layer also surrounds the medicament dispenser. The outer chemical barrier layer provides protection for the components stored within the interior of the package from exposure to contamination from hazardous chemical agents. The outer chemical barrier layer is preferably formed from a polyester material.

The protective package further includes at least one reinforcing layer secured to the outer chemical barrier layer. In accordance with the present invention, it is contemplated that the reinforcing layer may have several locations. First, the reinforcing layer may be positioned between the inner protective layer and the outer chemical barrier layer. Second, the reinforcing layer may be secured to an outer surface of the outer chemical barrier layer. Third, the reinforcing layer preferably includes a first reinforcing layer positioned between the inner protective layer and the outer chemical barrier layer and a second reinforcing layer surrounding an outer surface of the outer chemical barrier layer. Each reinforcing layer may be formed from a nylon material. The nylon material is preferably a biaxially oriented nylon material.

In accordance with the present invention, the protective package also provides protection against exposure to light. This is especially useful when, for example, the medicament stored within the package is light sensitive. The protective package may further include at least one light inhibiting layer for limiting the transmission of light through the protective package. The at least one light inhibiting layer may be formed from an ink layer printed on one of the inner protective layer, the at least one reinforcing layer and the outer chemical barrier layer.

The degree of protection against light transmission may not be uniform throughout the package. It may be necessary to provide additional protection against light transmission in areas of the package where a particularly light sensitive medicament is stored. This is especially important when the medicament dispenser stores atropine for use in the treatment of exposure to chemical nerve agents or other reagents that are light sensitive. The atropine is stored in a forward medicament storage compartment located in a forward portion of the medicament dispenser. 2-Pralidoxime chloride is stored in a second compartment behind the forward medicament storage compartment. The atropine and the 2-Pralidoxime chloride are mixed during the medicament administering operation. For inspection purposes, the atropine is visible through the medicament dispenser. As such, it is important to provide packaging that provides suitable protection against light transmission to prevent degradation of the atropine. It is especially important that the at least one light inhibiting layer be located on the protective package in the area surrounding the forward medicament storage compartment such that the forward medicament storage compartment is not visible when the medicament dispenser is located in the protective package. Although the present invention has been described in connection with atropine and 2-Pralidoxime chloride, other nerve agent antidotes and medicaments may be stored within the protective package.

Although 2-Pralidoxime chloride is not as light sensitive as atropine, it to a certain degree is light sensitive. As such, a protection against light transmission should be provided throughout the package. Typically, the medicament dispenser includes a label secured to the rearward portion of the dispenser in the area surrounding the 2-Pralidoxime chloride, which provides a certain amount of protection against light transmission. The label has certain valuable product information formed thereon, including but not limited to lot numbers, expiration dates and administering instructions. It is important that this information be visible through the protective package.

In accordance with the present invention, the at least one light inhibiting layer may include a first light inhibiting layer applied to one of the inner protective layer, the at least one reinforcing layer and the outer chemical barrier layer. The first light inhibiting layer preferably has a sufficient size such that the first light inhibiting layer surrounds the portion of the medicament dispenser storing the atropine. The first light inhibiting layer is preferably a layer of printed ink. The at least one light inhibiting layer may further include a second light inhibiting layer applied to one of the first light inhibiting layer, the inner protective layer, the at least one reinforcing layer and the outer chemical barrier layer. The second light inhibiting layer has a sufficient size such that the second light inhibiting layer surrounds the medicament dispenser. The product information on the label is visible through the second light inhibiting layer. The first light inhibiting layer covers a smaller area when compared to the second light inhibiting layer. The second light inhibiting layer also includes a printed ink. The ink forming the second layer is lighter than the ink formed the first light inhibiting layer.

In accordance with a preferred embodiment of the present invention, the protective package is formed as a laminated pouch. The protective package may be formed from a pair of laminated layers. Each laminated layer includes an inner protective layer, an outer chemical barrier layer secured to the inner protective layer, and at least one reinforcing layer secured to the outer chemical barrier layer. The at least one reinforcing layer may be positioned between the inner protective layer and the outer chemical barrier layer or secured to an outer surface of the outer chemical barrier layer. Preferably, the at least one reinforcing layer includes a first reinforcing layer positioned between the inner protective layer and the outer chemical barrier layer and a second reinforcing layer surrounding an outer surface of the outer chemical barrier layer. Each laminated layer includes an outer periphery extending around an outer edge of the laminated layer. A compartment periphery, which defines an outer edge of the storage compartment is spaced from the outer periphery. The medicament dispenser is located in the storage compartment. One of the pair of laminated layers is secured to another of the pair of laminated layers substantially across an area formed between the compartment periphery and the outer periphery.

The protective pouch preferably includes at least one light inhibiting layer for limiting the transmission of light through the protective package. The at least one light inhibiting layer is applied to one of the inner protective layer, the at least one reinforcing layer and the outer chemical barrier layer such that the least one light inhibiting layer extends substantially across the laminated layer to a point between the compartment periphery and the outer periphery. It is important that the light inhibiting layer does not extend to the outer periphery because this layer may have a negative impact on the bond formed between the laminated layers. The at least one light inhibiting layer may include a first light inhibiting layer applied to one of the inner protective layer, the at least one reinforcing layer and the outer chemical barrier layer. The first light inhibiting layer preferably has a sufficient size such that the first light inhibiting layer surrounds the portion of the medicament dispenser storing the atropine. The first light inhibiting layer is preferably a layer of printed ink. The at least one light inhibiting layer may further include a second light inhibiting layer applied to one of the first light inhibiting layer, the inner protective layer, the at least one reinforcing layer and the outer chemical barrier layer. The second light inhibiting layer has a sufficient size such that the second light inhibiting layer surrounds the entire medicament dispenser. The second light inhibiting layer also includes a printed ink. The ink forming the first layer is darker than the ink formed the second light inhibiting layer.

A plurality of notches may be formed between the outer periphery and the compartment periphery to facilitate opening of the compartment. Furthermore, a locator tab assembly is secured to one end of the protective package. The locator assembly provides a means for quickly orienting the protective package such that the medicament dispenser may be quickly removed for administering the medicament.

BRIEF DESCRIPTION OF THE DRAWINGS

The invention will be described in conjunction with the following drawing in which like reference numerals designate like elements and wherein.

DETAILED DESCRIPTION OF THE INVENTION

Figure 1:
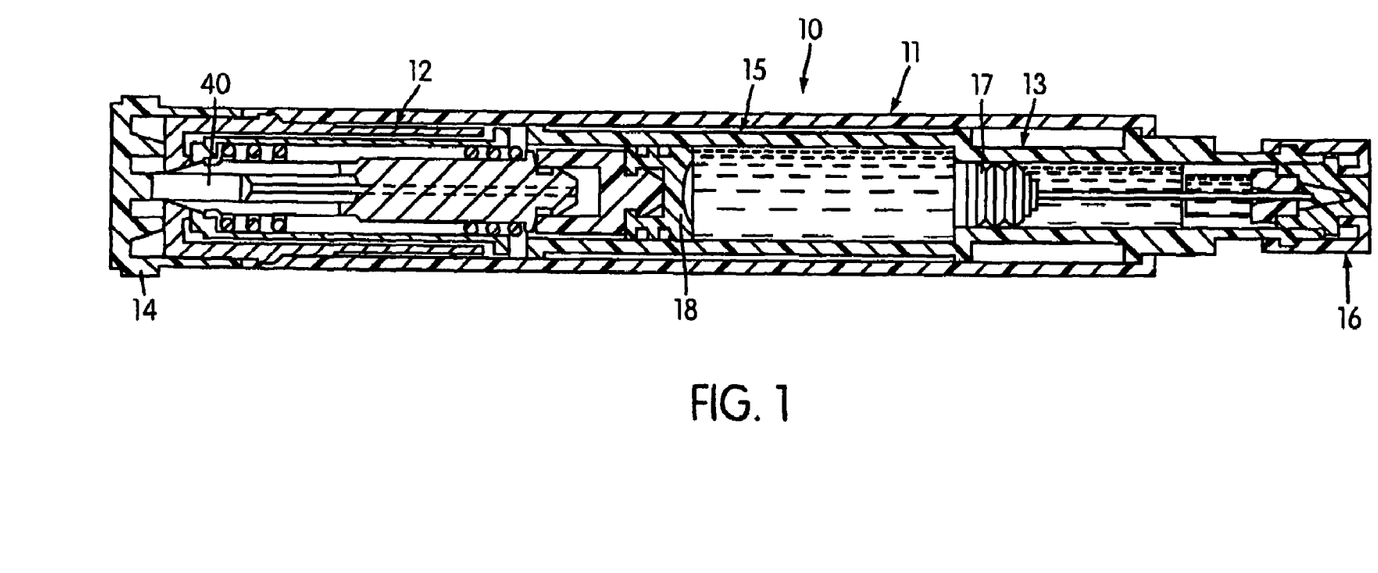
FIG. 1 is a cross sectional schematic view of a medicament dispenser assembly in accordance with an embodiment of the present invention.

A medicament dispenser 10 for use in connection with the protective packaging 20, described below, in accordance with the present invention is illustrated in FIG. 1 and described in greater detail in, for example, U.S. Pat. No. 5,092,843 to Monroe et al., entitled "Dispersion Multichamber Auto-Injector," the disclosure of which is specifically incorporated herein by reference. While the present invention will be described herein in connection with an autoinjector, the invention is not intended to be limited to use solely with autoinjectors. It is contemplated that the present invention may be used in connection with syringes, vials or any other type of device that is capable of administering and/or storing medicaments. The medicament dispenser 10 is an auto-injector having a housing member 11. A power pack assembly 12 is secured to a rearward end of the housing member 11 and operable in response to a predetermined manual actuating procedure to be released so as to operate a medicament injection cartridge assembly 13. The power pack assembly 12 includes a safety cap 14. The medicament cartridge assembly 13 includes a medicament container 15. A forward end portion of the container 15 is opened and closed by a closure assembly 16. It is contemplated that atropine will be stored within the forward end portion. A first piston 17 is slidably mounted within the container 15. A second piston 18 is mounted within a rear end portion of the container 15. The second piston 18 is disposed in slidable sealed relation with respect to the interior cylindrical surface of the container 15. The operation of the medicament dispenser 10 is disclosed in the '843 patent.

Figure 2:
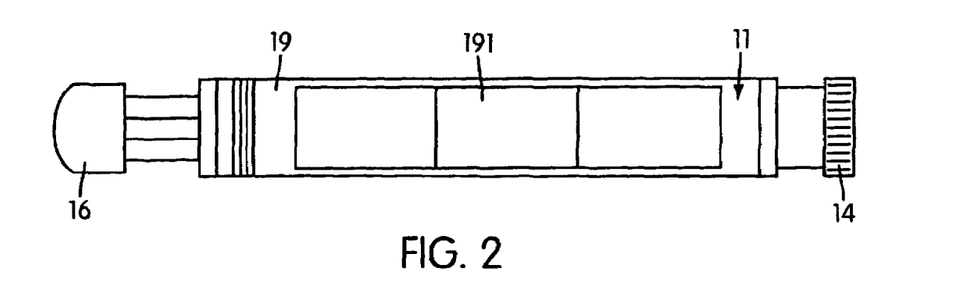
FIG. 2 is a schematic view of the medicament dispenser assembly of FIG. 1 illustrating a label having instructional information formed thereon.
Figure 3:
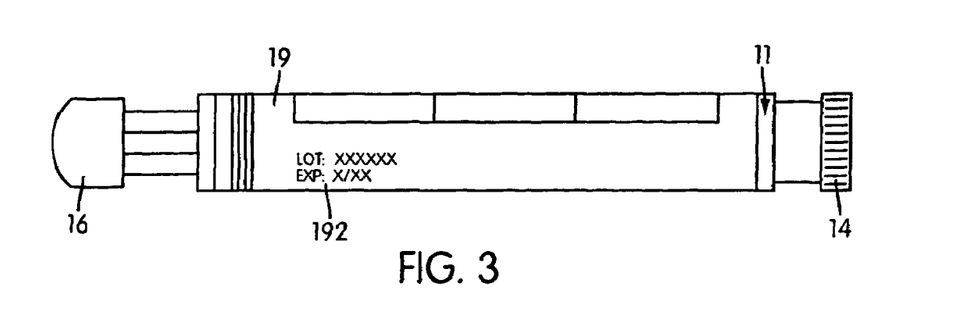
FIG. 3 is a schematic view of the medicament dispenser assembly of FIG. 2 illustrating another portion of the label having product information formed thereon.

It is intended that the medicament dispenser 10 is to be self-administered. It is also contemplated that the dispenser may be administered by a health care professional or another individual. It is also contemplated that the dispenser 10 be administered in the field (i.e., a battlefield), at home, the office, a sporting event. With that in mind, it is important that the medicament dispenser 10 include instructional information formed thereon. This information is located on a label 19 secured to the housing member 11. The label 19 may include step by step instructions 191 that can be easily viewed and followed in order to administer a dose of medicament, as shown in FIG. 2. It is contemplated that the medicament dispenser 10 will be used in connection with the administering of a reagent for use in the treatment of exposure to chemical nerve agents. The medicament may contain atropine and 2-Pralidoxime chloride stored therein. The label 19 will contain other valuable information 192 related to the medicament printed thereon, which may include expiration and lot information, as shown in FIG. 3. The present invention, however, is not limited to the use of reagents for the treatment of exposure to nerve agents; rather, numerous reagents are intended to be used in connection with the protective packaging including reagents for the treatment of bee stings, allergic reactions to food, etc.

It is anticipated that the medicament dispenser 10 will have many applications. The dispenser 10 may be carried by a soldier in the battlefield, an emergency relief worker or any individual that could potentially be exposed to chemical agents including chemical nerve agents. It therefore is important that the medicament dispenser 10 be protected from exposure to chemical contamination prior to use. Such contamination could have a negative impact of the medicament. While the present invention is disclosed in connection with the prevention of exposure to chemical agents, the protective packaging disclosed herein has numerous other applications including use in the prevention of light degradation of the medicament or exposure to other harmful contaminants.

Figure 4:
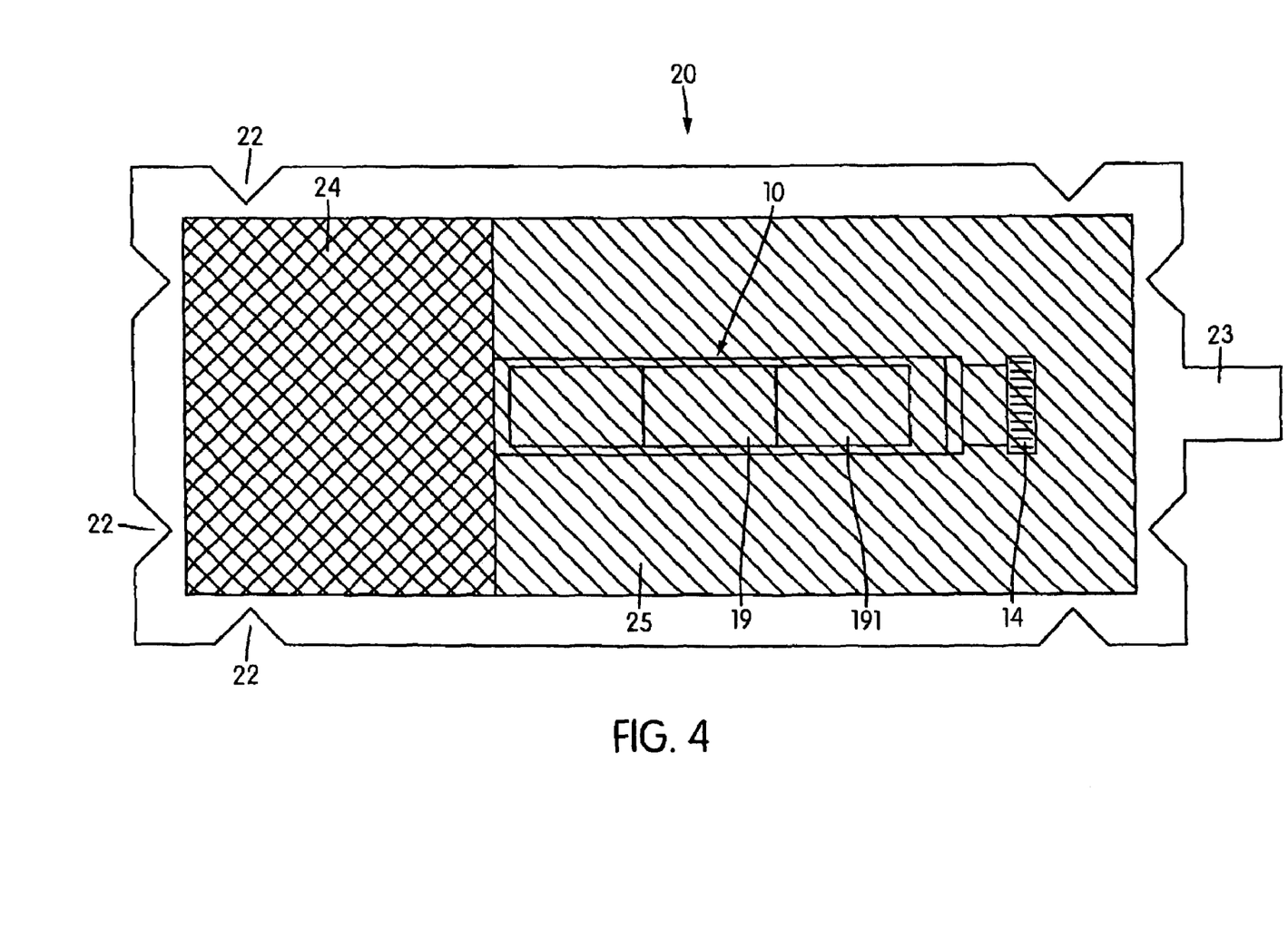
FIG. 4 is a schematic view of a protective packaging in accordance with the present invention having the medicament dispenser assembly of FIG. 2 located therein.
Figure 5:
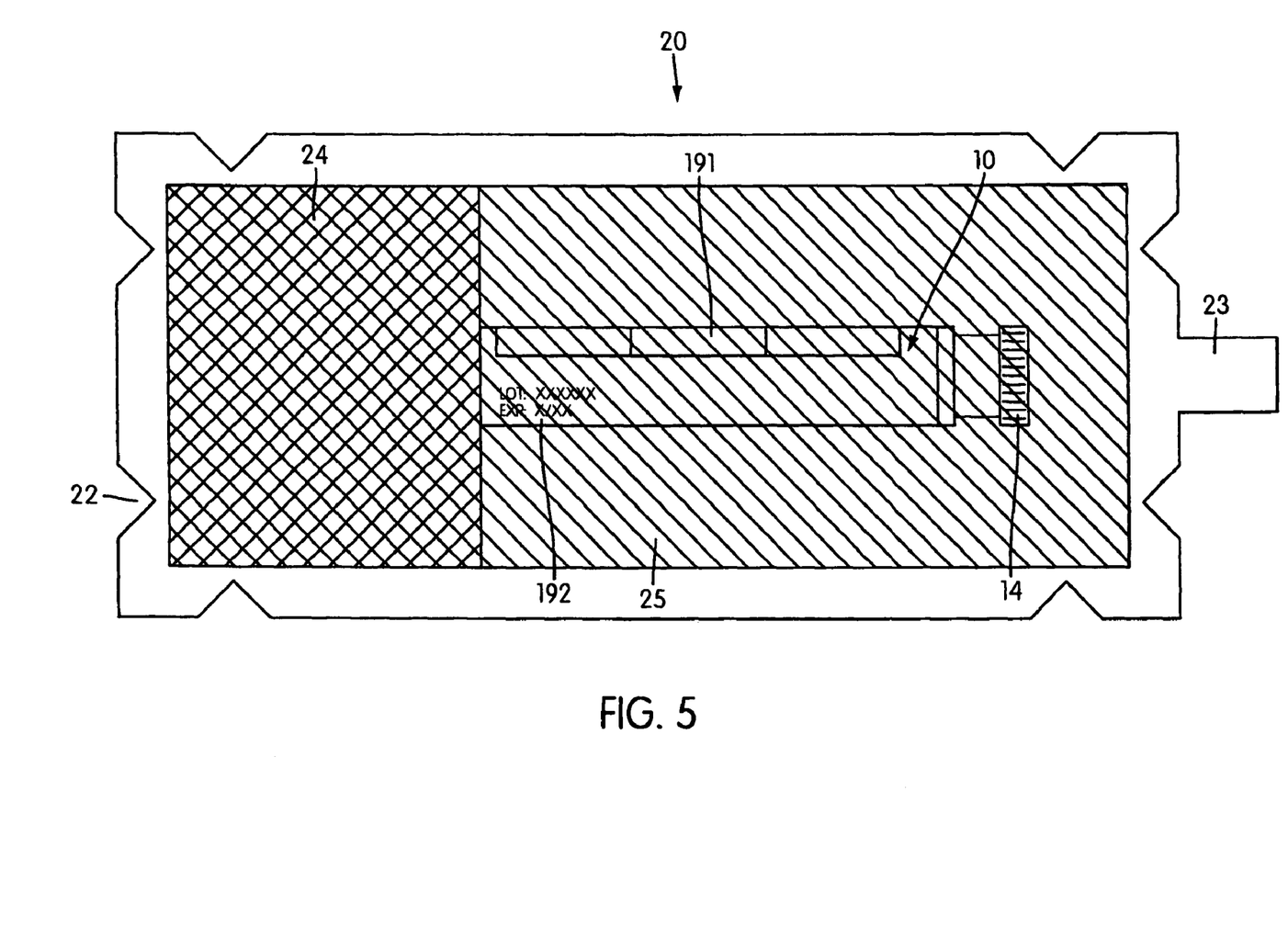
FIG. 5 is a schematic view of the protective packaging in accordance with the present invention illustrating the positioning of the label of the medicament dispenser assembly of FIG. 3 within the packaging.
Figure 6:
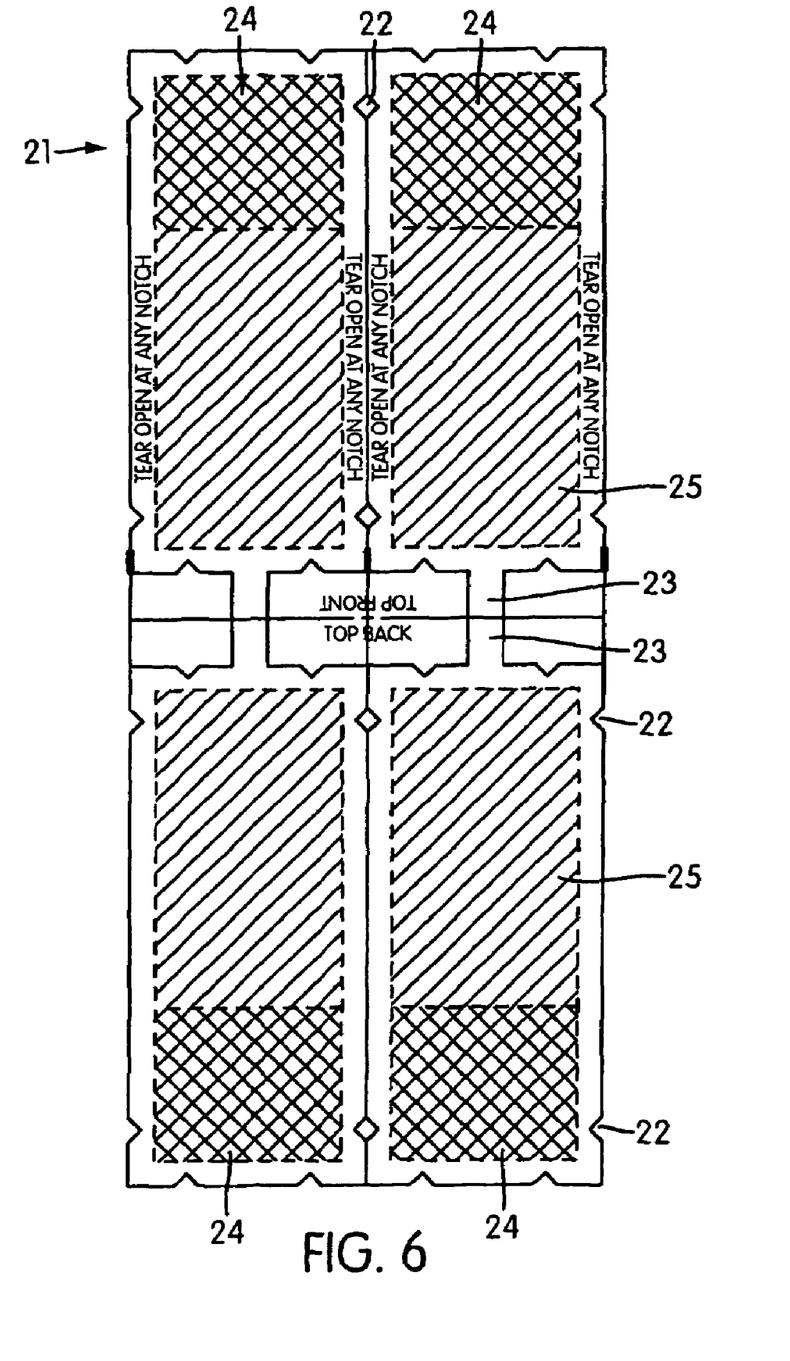
FIG. 6 is a schematic view of a sheet of materials forming the protective packaging in accordance with the present invention.
Figure 7:
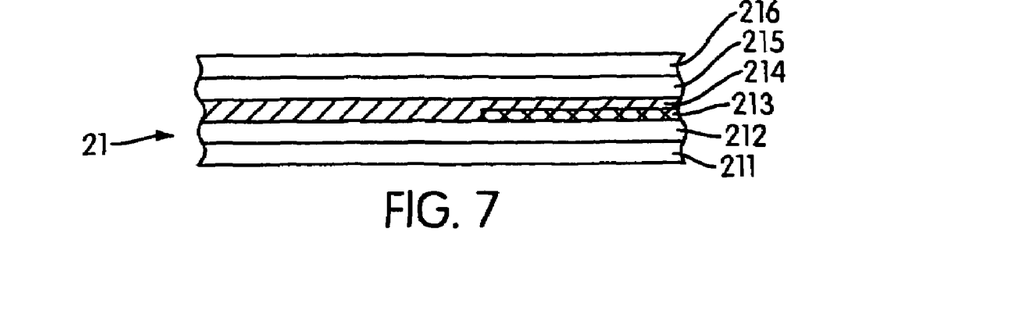
FIG. 7 is a partial side view illustrating the layers of material forming the protective packaging in accordance with the present invention.

A protective package 20 in accordance with one embodiment of the present invention will now be described in greater detail in connection with FIGS. 4-7, which provides suitable protection against contaminants, including but not limited to chemical contamination when exposed to chemical agents. The package 20 is preferably formed as a laminated pouch that is sized to receive the medicament dispenser 10 therein. The pouch 20 is formed from a laminated sheet 21. As shown in FIG. 6, the laminated sheet 21 may be used to form the front and back sheets for the pouch. It is contemplated that multiple pouches 20 may be formed from a single sheet, see FIG. 6. The construction of the laminated sheet 21 is illustrated in FIG. 7. The laminated sheet 21 includes an inner protective layer 211. The inner protective layer is arranged to be positioned adjacent the medicament dispenser 10 and forms the interior surface of the protective package 20. The layer 211 is preferably formed from a polyethylene material. Polyethylene is used because of its superior bonding properties when the front and back sheet are laminated or bonded together to form the package 20. The present invention, however, is not limited to the use of polyethylene; rather, it is contemplated that other materials may be used provided such material is capable of establishing a good bond or is capable of melting together during a lamination procedure and the material does not react with the other materials forming the sheet 21.

While the inner protective layer 211 forms a sealed water tight enclosure, the inner layer 211 does not provide adequate protection against contamination and exposure to hazardous chemical agents. The sheet 21 of the protective package 20 further includes an outer chemical barrier layer 215. The outer chemical barrier layer 215 provides protection against exposure to hazardous chemical nerve agents and the like. The chemical barrier layer 215 must also be able to withstand exposure to caustic cleaning agents including bleach and lye if a decontamination procedure on the package 20 is necessary. The outer chemical barrier layer 215 also surrounds the medicament dispenser. The outer chemical barrier layer 215 is preferably formed from a polyester material. The polyester material provides suitable protection against contamination. The polyester material which forms the layer 215 may sometimes be brittle, which may lead to a breakdown in the protection it provides, if the layer 215 cracks or separates from the layer 211. The present invention, however, is not limited to the use of polyester; rather, it is contemplated that other materials may be used provided such material is capable of maintaining a chemical barrier and does not breakdown when exposed to caustic cleaning agents.

In accordance with the present invention, at least one reinforcing layer 212 and 216 is provided to strengthen the outer chemical barrier layer 215, as shown in FIG. 7. The chemical barrier layer 215 is preferably sandwiched between reinforcing layers 212 and 216. A first reinforcing layer 212 is positioned between the inner protective layer 211 and the outer chemical barrier layer 215. A second reinforcing layer 216 is positioned on an outer surface of the outer chemical barrier layer 215. Each reinforcing layer 212 and 216 is formed from a nylon material. The nylon material is preferably a biaxially oriented nylon material. The biaxially oriented nylon material prevents cracking of the chemical barrier layer 215. Although the layer 21 is preferably formed with a pair of reinforcing layers 212 and 216, it is contemplated that one of the layers may be omitted. As such, it is possible to provide only layer 212 or layer 216. In field, the medicament dispenser 10 may be carried in a soldier's gas mask carrier, which may be abrasive. The outer layer 216 of nylon material provides a suitable layer of abrasion resistance when stored in this conditions. The present invention, however, is not limited solely for use in a soldier's gas mask carrier. The package 20 maybe located in a back pack or other suitable carrier. Furthermore, it is contemplated that a suitable fastener may be attached to the package 20 to facilitate carrying on belt or other article of clothing.

As discussed above, it is contemplated that the medicament dispenser 10 may store atropine and 2-Pralidoxime chloride. The present invention, however, is not limited to the use and storage of these components; various components that may or may not be light sensitive may b stored in the protective packaging described herein. Atropine and to a lesser degree the 2-Pralidoxime chloride are very sensitive to light. Light may cause these medicaments to break down and/or reduce the shelf life of the medicament. While it is possible to create a medicament dispenser 10 that inhibits light transmission, it is not desirable. Such a dispenser would prevent the visual inspection of the dispenser during fabrication. Additionally, it would prevent visual inspection of the medicament in the field, which is desirable. Atropine is a clear transparent liquid. A visual inspection of the portion of the medicament dispenser 10 housing the atropine prior to administering would confirm whether or not the atropine is suitable for injection. When the atropine solution is no longer colorless or transparent, this provides a visual indication to the user that the atropine may be contaminated or past its shelf life. Accordingly, it is necessary to provide the package 20 with protection against the transmission of light there through.

While it is desirable to provide protection against the transmission of light through the package 20, it is also desirable that at least a portion of the label 19, which contains instruction information 191 and medicament information 192 be visible through the package 20. As result, the degree of protection against light transmission may not be uniform throughout the package 20. It is necessary to provide increased protection against light transmission in the portion of the package 20 where the atropine is located (i.e., the forward end of the dispenser 10). The same degree of protection is not required for the rearward end of the dispenser 10 because 2-Pralidoxime chloride is less sensitive light and the label 19 provides a certain degree of protection from the light.

The protection against the transmission of light through the package 20 is provided by at least one light inhibiting layer 213 and 214. A first light inhibiting layer 213 is applied to one of the inner protective layer 211, the at least one reinforcing layer 212 and 216 and the outer chemical barrier layer 215. As, shown in FIGS. 4, 5 and 6, the first light inhibiting layer 213 is sized to cover the area surrounding the front portion of the dispenser 10. The first light inhibiting layer 213 is preferably formed from at least one layer of printed ink. The ink is preferably a black ink to prevent the passage of light there through. A second light inhibiting layer 216 is applied over the first light inhibiting layer 213. The second light inhibiting layer 213 extends over the entire area forming the interior of the pouch 20, as shown in FIGS. 4, 5 and 6. The product information 191 and 192 on the label 19 is visible through the second light inhibiting layer 214. The second light inhibiting layer 214 covers a larger area than the first layer 214. The ink forming the second layer 214 is lighter than the first layer and is preferably amber in color. As can be seen from FIGS. 4, 5 and 6, the light inhibiting layers 213 and 214 do not extend to the outer periphery of the package 20; rather, the edges of the layers 213 and 214 are spaced from the outer periphery. It has been found that the extension of the layers 213 and 214 to the outer periphery adversely impacts the bond formed between the individual layers 211, 212, 215 and 216.

A plurality of notches 22 may be formed along the outer periphery of the package 20, as shown in FIGS. 4, 5 and 6. The notches 22 are sized such they do not extend into the interior of the package 20. The notches 22 are provided to facilitate opening of the package 20. While a notch has been disclosed, it is contemplated that other means for facilitating opening of the package 20 may be provided include a perforation and a tear strip.

It is contemplated that the user of the medicament dispenser 10 may not always be able to clearly view the package 20 (i.e., during night use). As such, it is necessary to provide a locator assembly 23 in the form of a tab on one of the package 20 As shown in FIG. 6, the locator assembly 23 is integrally formed with the layer 21. The tab 23 is located at end opposite the front end of the medicament dispenser 10. As such, the user of the dispenser 10 can correctly orient the dispenser 10 by holding the tab 23 whereby the front end of the dispenser 10 will be located away from the hand of the user.

As shown in FIG. 6, two layers 21 form the package 20. The layers 21 are aligned and heat sealed along three edges. A fourth edge is left unsealed such that the medicament dispenser 10 maybe inserted. The package 20 is sized such the movement of the dispenser 10 within the package 20 is limited. The front portion of the dispenser 10 housing the atropine is located under the area 24 created by the first light inhibiting layer 213. The package 20 and the area 24 is sized such that the front portion of the dispenser 10 will not be exposed to light, as shown in FIGS. 4 and 5. A portion of the label 19 is also covered by the area 24. The remaining portion of the label 19 is located in the area 25 formed by the second light inhibiting layer 214. None of the indicia 191 and 192 are covered by the area 24. After the dispenser 10 is properly located within the package 20, the remaining edge is sealed. All of the sealed edges must be liquid and gas tight.

Figure 8:
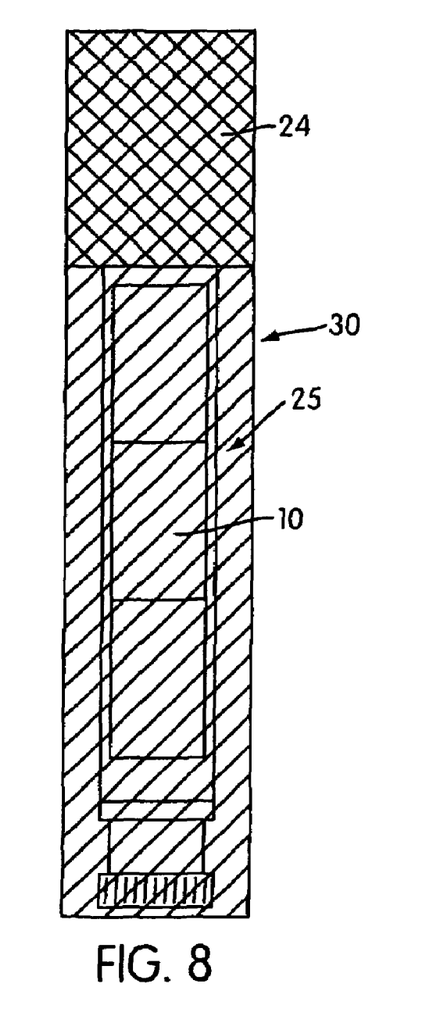
FIG. 8 is a schematic view of a protective packaging in accordance with another embodiment of the present invention.

It will be apparent to those skilled in the art that various modifications and variations may be made without departing from the scope of the present invention. For example, the present invention has been described above as a pouch 20. The present invention is not intended to be so limiting; rather is contemplated that the protective packaging in accordance with the present invention may take the form of protective cylinder 30, as shown in FIG. 8. The cylinder 30 is formed of a single layer 21 secured together along one edge. One end of the cylinder 30 is sealed. An opposite end may include a removable panel to permit access to the medicament dispenser 10 stored therein. It is contemplated that a gas absorbing material may be located within the package 20 to absorb any gas trapped within the package during the sealing operation. It is intended that the present invention covers the modifications and variations of the invention, provided they come within the scope of the appended claims and their equivalents.

What is claimed is:

1. A protective package for a medicament dispenser that contains at least one medicament stored therein, the protective package comprising:
    an inner protective layer surrounding the medicament dispenser;
    an outer chemical barrier layer disposed about the inner protective layer that surrounds the medicament dispenser and protects the medicament dispenser from chemical contamination,
    a light inhibiting layer of printed ink applied to the inner protective layer or the outer chemical barrier layer, the printed ink completely covering at least about an upper or lower third of the inner protective layer or the outer chemical barrier layer, the light inhibiting layer limiting the transmission of light through the protective package; and
    at least one reinforcing layer disposed about the outer chemical barrier layer.

2. The protective package according to claim 1 further comprising a second reinforcing layer positioned between the inner protective layer and the outer chemical barrier layer.

3. The protective package according to claim 2 wherein the at least one reinforcing layer is formed from a biaxially oriented nylon material.

4. The protective package according to claim 1, wherein the at least one reinforcing layer is secured to an outer surface of the outer chemical barrier layer.

5. The protective package according to claim 4, wherein the at least one reinforcing layer is formed from a biaxially oriented nylon material.

6. The protective package according to claim 1, wherein the at least one reinforcing layer includes a first reinforcing layer positioned between the inner protective layer and the outer chemical barrier layer and a second reinforcing layer surrounding an outer surface of the outer chemical barrier layer.

7. The protective package according to claim 6, wherein each reinforcing layer is formed from a biaxially oriented nylon material.

8. The protective package according to claim 1, wherein the inner protective layer is formed from a polyethylene material.

9. The protective package according to claim 1, wherein the outer chemical barrier layer is formed from a polyester material.

10. The protective package according to claim 1, wherein the light inhibiting layer limits the transmission of light nonuniformly through the protective package.

11. The protective package according to claim 1, wherein the light inhibiting layer includes a black or amber printed ink layer.

12. The protective package according to claim 10, further comprising a second reinforcing layer secured to the inner protective layer.

13. The protective package according to claim 2, wherein the light inhibiting layer is applied to one of the inner protective layer, the second reinforcing layer and the outer chemical barrier layer.

14. The protective package according to claim 1, wherein the medicament dispenser includes a forward portion, a rearward portion, and a forward medicament storage compartment located in the forward portion, the light inhibiting layer located on the protective package in the area surrounding the forward medicament storage compartment such that the forward medicament storage compartment is not visible when the medicament dispenser is located in the protective package.

15. The protective package according to claim 14, wherein the medicament dispenser includes a label secured to the rearward portion, the label having product information formed thereon that is visible through the protective package.

16. The protective package according to claim 14, wherein the light inhibiting layer comprises:
    a first light inhibiting layer applied to one of the inner protective layer and the outer chemical barrier layer, wherein the first light inhibiting layer has a sufficient size such that the first light inhibiting layer surrounds the forward medicament storage compartment, and
    a second light inhibiting layer applied to one of the first light inhibiting layer, the inner protective layer, and the outer chemical barrier layer, wherein the second light inhibiting layer has a sufficient size such that the second light inhibiting layer surrounds the medicament dispenser.

17. The protective package according to claim 16, wherein the medicament dispenser includes a label secured to the rearward portion, the label having product information formed thereon that is visible through the protective package.

18. The protective package according to claim 16, wherein the first light inhibiting layer includes a first printed ink layer and the second light inhibiting layer includes a second printed ink layer, wherein the first printed ink layer is darker than the second printed ink layer.

19. The protective package according to claim 16, further comprising a locator assembly secured to one end of the protective package, wherein the locator assembly locates an end of the protective package opposite the forward medicament storage compartment.

20. The protective package according to claim 1, wherein the protective package is formed from a pair of laminated layers, wherein each laminated layer comprises:
    the inner protective layer;
    the outer chemical barrier layer secured to the inner protective layer, and
    at least one reinforcing layer secured to the outer chemical barrier layer.

21. The protective package according to claim 20 further comprising a second reinforcing layer positioned between the inner protective layer and the outer chemical barrier layer.

22. The protective package according to claim 20, wherein the at least one reinforcing layer is secured to an outer surface of the outer chemical barrier layer.

23. The protective package according to claim 20, wherein the at least one reinforcing layer includes a first reinforcing layer positioned between the inner protective layer and the outer chemical barrier layer and a second reinforcing layer surrounding an outer surface of the outer chemical barrier layer.

24. The protective package according to claim 20, wherein the light inhibiting layer limits the transmission of light nonuniformly through the protective package.

25. The protective package according to claim 24, wherein each laminated layer comprises:
an outer periphery extending around an outer edge of the laminated layer; and
a compartment periphery spaced from the outer periphery, wherein the compartment periphery defines an outer edge of a storage compartment and the medicament dispenser is located in the storage compartment.

26. The protective package according to claim 25, wherein the light inhibiting layer extends substantially across the laminated layer to a point between the compartment periphery and the outer periphery.

27. The protective package according to claim 26, wherein one of the pair of laminated layers is secured to another of the pair of laminated layers substantially across an area formed between the compartment periphery and the outer periphery.

28. The protective package according to claim 27, further comprising opening means for facilitating opening of the protective pouch, wherein the opening means being located in the area between the outer periphery and the compartment periphery.

29. The protective package according to claim 20, wherein the medicament dispenser includes a forward portion, a rearward portion, and a forward medicament storage compartment located in the forward portion, the light inhibiting layer located on the protective package in the area surrounding the forward medicament storage compartment such that the forward medicament storage compartment is not visible when the medicament dispenser is located in the protective package.

30. The protective package according to claim 29, wherein the medicament dispenser includes a label secured to the rearward portion, the label having product information formed thereon that is visible through the protective package.

31. The protective package according to claim 30, wherein the light inhibiting layer comprises:
a first light inhibiting layer applied to one of the inner protective layer, the at least one reinforcing layer and the outer chemical barrier layer, wherein the first light inhibiting layer has a sufficient size such that the first light inhibiting layer surrounds the forward medicament storage compartment; and
a second light inhibiting layer applied to one of the first light inhibiting layer, the inner protective layer, the at least one reinforcing layer and the outer chemical barrier layer, wherein the second light inhibiting layer has a sufficient size such that the second light inhibiting layer surrounds the medicament dispenser.

32. The protective package according to claim 1, wherein the medicament dispenser includes a label having product information formed thereon that is visible through the protective package.

33. The protective package according to claim 31, wherein the first light inhibiting layer includes a first printed ink layer and the second light inhibiting layer includes a second printed ink layer, wherein the first printed ink layer is darker than the second printed ink.

34. A medicament dispenser for dispensing at least one medicament in combination with a protective package for storing the medicament dispenser, the medicament dispenser comprising:
a housing having a forward portion and a rearward portion; and
a forward medicament storage compartment for storing the at least one medicament therein, the forward medicament storage compartment located in the forward portion,
the protective package comprising:
an inner protective layer surrounding the medicament dispenser;
an outer chemical barrier layer disposed about the inner protective layer, wherein the outer chemical barrier layer surrounds the medicament dispenser and protects the medicament dispenser from chemical contamination;
at least one light inhibiting layer of printed ink applied to the inner protective layer or the outer chemical barrier layer, the printed ink completely covering at least the portion of the inner protective layer or the outer chemical barrier layer that lays over the forward portion of the dispenser housing, the light inhibiting layer limiting the transmission of light through the protective package; and
at least one reinforcing layer disposed about the outer chemical barrier layer.

35. The combination according to claim 34, wherein a second reinforcing layer is positioned between the inner protective layer and the outer chemical barrier layer.

36. The combination according to claim 35, wherein the at least one reinforcing layer is formed from a biaxially oriented nylon material.

37. The combination according to claim 34, wherein the at least one reinforcing layer is secured to an outer surface of the outer chemical barrier layer.

38. The combination according to claim 37, wherein the at least one reinforcing layer is formed from a biaxially oriented nylon material.

39. The combination according to claim 34, wherein the at least one reinforcing layer includes a first reinforcing layer positioned between the inner protective layer and the outer chemical barrier layer and a second reinforcing layer surrounding an outer surface of the outer chemical barrier layer.

40. The combination according to claim 39, wherein each reinforcing layer is formed from a biaxially oriented nylon material.

41. The combination according to claim 34, wherein the inner protective layer is formed from a polyethylene material.

42. The combination according to claim 34, wherein the outer chemical barrier layer is formed from a polyester material.

43. The combination according to claim 34, wherein the light inhibiting layer limits the transmission of light nonuniformly through the protective package.

44. The combination according to claim 34, wherein the light inhibiting layer includes a black or amber printed ink layer.

45. The combination according to claim 44, further comprising at least one reinforcing layer secured to the outer chemical barrier layer.

46. The combination according to claim 35, wherein the light inhibiting layer is applied to one of the inner protective layer, the second reinforcing layer and the outer chemical barrier layer.

47. The combination according to claim 34, wherein:
a light sensitive medicament is stored in the forward medicament storage compartment, the light sensitive medicament is visible through the forward medicament storage compartment, the light inhibiting layer is located on the protective package in the area surrounding the forward medicament storage compartment, and the forward medicament storage compartment is not visible when the medicament dispenser is located in the protective package.

48. The combination according to claim 47, wherein the medicament dispenser includes a label secured to the rearward portion, the label having product information formed thereon that is visible through the protective package.

49. The combination according to claim 34, wherein the light inhibiting layer comprises:

a first light inhibiting layer applied to one of the inner protective layer, the at least one reinforcing layer and the outer chemical barrier layer, wherein the first light inhibiting layer has a sufficient size such that the first light inhibiting layer surrounds the forward medicament storage compartment, and a second light inhibiting layer applied to one of the first light inhibiting layer, the inner protective layer, the at least one reinforcing layer and the outer chemical barrier layer, wherein the second light inhibiting layer has a sufficient size such that the second light inhibiting layer surrounds the medicament dispenser.

50. The combination according to claim 49, wherein the medicament dispenser includes a label secured to the rearward portion, the label having product information formed thereon that is visible through the protective package.

51. The combination according to claim 50, wherein the first light inhibiting layer includes a first printed ink layer and the second light inhibiting layer includes a second printed ink layer, wherein the first printed ink layer is darker than the second printed ink layer.

52. The combination according to claim 50, further comprising a locator assembly secured to one end of the protective package, wherein the locator assembly locates an end of the protective package opposite the forward medicament storage compartment.

53. The combination according to claim 34, wherein the protective package is formed from a pair of laminated layers, wherein each laminated layer comprises:

the inner protective layer;

the outer chemical barrier layer secured to the inner protective layer; and at least one reinforcing layer secured to the outer chemical barrier layer.

54. The combination according to claim 53, wherein the at least one reinforcing layer is positioned between the inner protective layer and the outer chemical barrier layer.

55. The combination according to claim 53, wherein the at least one reinforcing layer is secured to an outer surface of the outer chemical barrier layer.

56. The combination according to claim 53, wherein the at least one reinforcing layer includes a first reinforcing layer positioned between the inner protective layer and the outer chemical barrier layer and a second reinforcing layer surrounding an outer surface of the outer chemical barrier layer.

57. The combination according to claim 53, wherein the light inhibiting layer limits the transmission of light non-uniformly through the protective package.

58. The combination according to claim 57, wherein each laminated layer comprises:

an outer periphery extending around an outer edge of the laminated layer; and a compartment periphery spaced from the outer periphery, wherein the compartment periphery defines an outer edge of a storage compartment and the medicament dispenser is located in the storage compartment.

59. The combination according to claim 58, wherein the light inhibiting layer is applied to one of the inner protective layer and the outer chemical barrier layer such that the light inhibiting layer extends substantially across the laminated layer to a point between the compartment periphery and the outer periphery.

60. The combination according to claim 59, wherein one of the pair of laminated layers is secured to another of the pair of laminated layers substantially across an area formed between the compartment periphery and the outer periphery.

61. The combination according to claim 59, wherein:

a light sensitive medicament is stored in the forward medicament storage compartment, the light sensitive medicament is visible through the forward medicament storage compartment, the light inhibiting layer is located on the protective package in the area surrounding the forward medicament storage compartment, and the forward medicament storage compartment is not visible when the medicament dispenser is located in the protective package.

62. The combination according to claim 61, wherein the medicament dispenser includes a label secured to the rearward portion, the label having product information formed thereon that is visible through the protective package.

63. The combination according to claim 62, wherein the light inhibiting layer comprises:

a first light inhibiting layer applied to one of the inner protective layer, the at least one reinforcing layer and the outer chemical barrier layer, wherein the first light inhibiting layer has a sufficient size such that the first light inhibiting layer surrounds the forward medicament storage compartment; and a second light inhibiting layer applied to one of the first light inhibiting layer, the inner protective layer, the at least one reinforcing layer and the outer chemical barrier layer, wherein the second light inhibiting layer has a sufficient size such that the second light inhibiting layer surrounds the medicament dispenser.

64. The combination according to claim 34, wherein the medicament dispenser includes a label having product information formed thereon that is visible through the protective package.

65. The combination according to claim 63, wherein the first light inhibiting layer includes a first printed ink layer and the second light inhibiting layer includes a second printed ink layer, wherein the first printed ink layer is darker than the second printed ink layer.

* * * * *